United States Patent
Steiger et al.

(10) Patent No.: US 9,650,396 B2
(45) Date of Patent: May 16, 2017

(54) INDIUM OXOALKOXIDES FOR PRODUCING COATINGS CONTAINING INDIUM OXIDE

(75) Inventors: Juergen Steiger, Duesseldorf (DE); Duy Vu Pham, Oberhausen (DE); Heiko Thiem, Bensheim (DE); Alexey Merkulov, Ludwigshafen (DE); Arne Hoppe, Herne (DE)

(73) Assignee: Evonik Degussa GmbH, Essen (DE)

( * ) Notice: Subject to any disclaimer, the term of this patent is extended or adjusted under 35 U.S.C. 154(b) by 851 days.

(21) Appl. No.: 13/809,423

(22) PCT Filed: Jul. 12, 2011

(86) PCT No.: PCT/EP2011/061867
§ 371 (c)(1),
(2), (4) Date: Jan. 10, 2013

(87) PCT Pub. No.: WO2012/010464
PCT Pub. Date: Jan. 26, 2012

(65) Prior Publication Data
US 2013/0104773 A1    May 2, 2013

(30) Foreign Application Priority Data

Jul. 21, 2010  (DE) .......... 10 2010 031 895

(51) Int. Cl.
*H01B 1/00* (2006.01)
*C23C 16/40* (2006.01)
(Continued)

(52) U.S. Cl.
CPC .............. *C07F 5/003* (2013.01); *C07C 31/28* (2013.01); *C09D 1/00* (2013.01); *C23C 18/1216* (2013.01)

(58) Field of Classification Search
CPC ...... C23C 18/1216; C23C 16/407; C09D 1/00
(Continued)

(56) References Cited

U.S. PATENT DOCUMENTS 5,237,081 A * 8/1993 Moore .................... C07C 29/70
556/1
2009/0112012 A1* 4/2009 Leedham .............. C07C 29/685
556/136

(Continued)

FOREIGN PATENT DOCUMENTS

WO    2011 020781    2/2011
WO    2011 072887    6/2011
(Continued)

OTHER PUBLICATIONS

U.S. Appl. No. 13/516,900, filed Aug. 6, 2012, Steiger, et al.
(Continued)

*Primary Examiner* — Bijan Ahvazi
*Assistant Examiner* — Thuy-Ai N Nguyen
(74) *Attorney, Agent, or Firm* — Oblon, McClelland, Maier & Neustadt, L.L.P.

(57) ABSTRACT

The present invention relates to halogenated indium oxo alkoxides of the generic formula $In_7O_2(OH)(OR)_{12}X_4(ROH)_x$ where R=C1-C15-alkyl, C1-C15-alkenyl, C1-C15-alkynyl, C1-C15-alkoxyalkyl, C6-C15-aryl- or C7-C15-alkoxyaryl, X=F, Cl, Br, I and x=0 to 10, to processes for preparation thereof and to use thereof.

19 Claims, 1 Drawing Sheet

Structural formula $In_7(\mu_4\text{-}O)_2(\mu_2\text{-}OH)(\mu_1\text{-}OEt)_3(\mu_2\text{-}OEt)_7(\mu_3\text{-}OEt)_2(\mu_1\text{-}Cl)_4$
R = Et

(51) Int. Cl.
*C23C 18/12* (2006.01)
*C09D 1/00* (2006.01)
*C07F 5/00* (2006.01)
*C07C 31/28* (2006.01)

(58) Field of Classification Search
USPC .......................................................... 252/500
See application file for complete search history.

(56) References Cited

U.S. PATENT DOCUMENTS

| 2010/0132788 | A1 | 6/2010 | Petrat et al. | |
|---|---|---|---|---|
| 2011/0193084 | A1 | 8/2011 | Thiem et al. | |
| 2011/0309313 | A1 | 12/2011 | Steiger et al. | |
| 2011/0315982 | A1 | 12/2011 | Hoppe et al. | |
| 2012/0181488 | A1 | 7/2012 | Steiger et al. | |
| 2012/0202318 | A1* | 8/2012 | Steiger et al. | 438/104 |
| 2012/0213980 | A1 | 8/2012 | Arning et al. | |
| 2012/0289728 | A1 | 11/2012 | Steiger et al. | |
| 2013/0104773 | A1 | 5/2013 | Steiger et al. | |
| 2015/0053966 | A1 | 2/2015 | Steiger et al. | |

FOREIGN PATENT DOCUMENTS

| WO | 2011 073005 | 6/2011 |
|---|---|---|
| WO | 2012 010427 | 1/2012 |
| WO | 2012 010464 | 1/2012 |
| WO | 2012 062575 | 5/2012 |

OTHER PUBLICATIONS

U.S. Appl. No. 13/809,322, filed Jan. 9, 2013, Steiger, et al.
D. C. Bradley et al., "Pentanuclear Oxoalkoxide Clusters of Scandium, Yttrium, Indium and Ytterbium, X-Ray Crystal Structures of $[M_5(\mu_5\text{-}O)(\mu_3\text{-}OPr^i)_4(\mu_2\text{-}OPr^i)_4(OPr^i)_5]$ (M=In, Yb)", Polyhedron, vol. 9, No. 5, 1990, pp. 719-726.
Duan Tai-Ke et al., "Synthesis and Crystal Structure of a Novel Hexanuclear Copper-indium Thiolate Complex $[(InCl)_2(\text{ OMe })(\mu\text{-OMe })_2(\mu_3\text{-OMe})(\mu\text{-SPr}'')_2(\text{ CuPPh}_3)]_2$", Chinese J. Struct. Chem., vol. 28, No. 5, 2009, pp. 565-568.
U.S. Appl. No. 13/884,495, filed May 9, 2013, Steiger, et al.
U.S. Appl. No. 14/407,681, filed Dec. 12, 2014, Steiger, et al.
Kim, H., et al., "High Performance Solution-Processed Indium Oxide Thin-Film Transistors," J. Am. Chem. Soc., vol. 130, pp. 12580 to 12581, (2008) XP 002613079.
Chamazi, N., et al., "Reaktionen von MeInCl2 mit Lithiumalkoholaten," Z. Anorg. Alig. Chem., vol. 633, pp. 2154 to 2158, (2007) XP 55008632.
International Search Report Issued Oct. 11, 2011 in PCT/EP11/061867 Filed Jul. 12, 2011.

* cited by examiner

Structural formula $In_7(\mu_4\text{-}O)_2(\mu_2\text{-}OH)(\mu_1\text{-}OEt)_3(\mu_2\text{-}OEt)_7(\mu_3\text{-}OEt)_2(\mu_1\text{-}Cl)_4$
R = Et
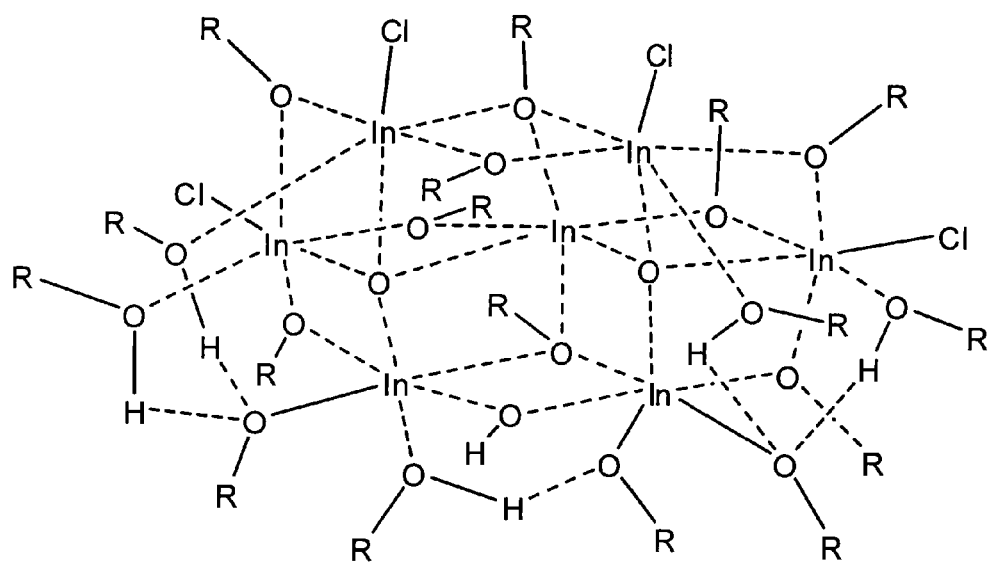

INDIUM OXOALKOXIDES FOR PRODUCING COATINGS CONTAINING INDIUM OXIDE

The present invention relates to indium oxo alkoxides for the production of indium oxide-containing layers, to processes for preparation thereof and to use thereof, especially for production of indium oxide-containing layers, as a constituent of coating compositions and for production of electronic components.

Indium oxide (indium(III) oxide, $In_2O_3$), owing to the large band gap between 3.6 and 3.75 eV (measured for vapour-deposited layers) [H. S. Kim, P. D. Byrne, A. Facchetti, T. J. Marks; *J. Am. Chem. Soc.* 2008, 130, 12580-12581], is a promising semiconductor. Thin films of a few hundred nanometers in thickness may additionally have a high transparency in the visible spectral range of greater than 90% at 550 nm. In extremely highly ordered single indium oxide crystals, it is additionally possible to measure charge carrier mobilities of up to 160 $cm^2/Vs$.

Indium oxide is often used in particular together with tin(IV) oxide ($SnO_2$) as the semiconductive mixed oxide ITO. Owing to the comparatively high conductivity of ITO layers with simultaneous transparency in the visible spectral range, one application thereof is in the field of liquid-crystal displays (LCDs), especially as a "transparent electrode". These usually doped metal oxide layers are produced industrially in particular by costly vapour deposition methods under high vacuum.

Indium oxide-containing layers and the production thereof, especially ITO layers and pure indium oxide layers, and the production thereof, are thus of great significance for the semiconductor and display industry.

Possible reactants and precursors discussed for the synthesis of indium oxide-containing layers include a multitude of compound classes. Examples include indium salts. For instance, Marks et al. describe components produced using a precursor solution composed of $InCl_3$ and the base monoethanolamine (MEA) dissolved in methoxyethanol. After spin-coating of the solution, the corresponding indium oxide layer is obtained by thermal treatment at 400° C. [H. S. Kim, P. D. Byrne, A. Facchetti, T. J. Marks; *J. Am. Chem. Soc.* 2008, 130, 12580-12581 and supplemental information].

Elsewhere, possible reactants or precursors discussed for the indium oxide synthesis are indium alkoxides. An indium alkoxide is a compound consisting of at least one indium atom, at least one alkoxide radical of the formula —OR (R=organic radical) and optionally one or more organic radicals —R, one or more halogen radicals and/or one or more —OH or —OROH radicals.

Independently of a possible use for indium oxide formation, the prior art describes various indium alkoxides and indium oxo alkoxides. Compared to the indium alkoxides already mentioned, indium oxo alkoxides also have at least one further oxygen radical (oxo radical) bound directly to an indium atom or bridging at least two indium atoms.

Mehrotra et al. describe the preparation of indium trisalkoxide $In(OR)_3$ from indium(III) chloride ($InCl_3$) with Na—OR where R is methyl, ethyl, isopropyl, n-, s-, t-butyl and pentyl radicals. [S. Chatterjee, S. R. Bindal, R. C. Mehrotra; *J. Indian Chem. Soc.* 1976, 53, 867].

A review article by Carmalt et al. (Coordination Chemistry Reviews 250 (2006), 682-709) describes various gallium(III) and indium(III) alkoxides and aryloxides, some of which may also be present with bridging by means of alkoxide groups. Additionally presented is an oxo-centred cluster of the formula $In_5(\mu\text{-}O)(O^iPr)_{13}$, more specifically $[In_5(\mu_5\text{-}O)(\mu_3\text{-}O^iPr)_4(\mu_2\text{-}O^iPr)_4(O^iPr)_5]$, which is an oxo alkoxide and cannot be prepared from $[In(O^iPr)_3]$.

A review article by N. Turova et al., Russian Chemical Reviews 73 (11), 1041-1064 (2004) summarizes synthesis, properties and structures of metal oxo alkoxides, which are considered therein as precursors for the production of oxidic materials via sol-gel technology. In addition to a multitude of other compounds, the synthesis and structure of $[Sn_3O(O^tBu)_{10}(^tBuOH)_2]$, of the already mentioned compound $[In_5O(O^iPr)_{13}]$ and of $[Sn_6O_4(OR)_4]$ (R=Me, $Pr^i$) are described.

The article by N. Turova et al., Journal of Sol-Gel Science and Technology, 2, 17-23 (1994) presents results of studies on alkoxides, which are considered therein as a scientific basis for the development of sol-gel processes of alkoxides and alkoxide-based powders. In this context, there is also discussion of a purported "indium isopropoxide", which was found to be the oxo alkoxide with a central oxygen atom and five surrounding metal atoms of the formula $M_5(\mu\text{-}O)(O^iPr)_{13}$ which is also described in Carmalt et al.

A synthesis of this compound and the crystal structure thereof are described by Bradley et al., J. Chem. Soc., Chem. Commun., 1988, 1258-1259. Further studies by the authors led to the result that the formation of this compound cannot be attributed to a hydrolysis of intermediately formed $In(O^iPr)_3$ (Bradley et al., Polyhedron Vol. 9, No. 5, pp. 719-726, 1990). Suh et al., J. Am. Chem. Soc. 2000, 122, 9396-9404 additionally found that this compound is not preparable by a thermal route either from $In(O^iPr)_3$. Moreover, Bradley (Bradley et al., Polyhedron Vol. 9, No. 5, pp. 719-726, 1990) found that this compound cannot be sublimed.

Metal oxide layers can in principle be produced via various processes.

One means of producing metal oxide layers is based on sputtering techniques. However, these techniques have the disadvantage that they have to be performed under high vacuum. A further disadvantage is that the films produced therewith have many oxygen defects, which make it impossible to establish a controlled and reproducible stoichiometry of the layers and hence lead to poor properties of the layers produced.

Another means in principle for producing metal oxide layers is based on chemical gas phase deposition. For example, it is possible to produce indium oxide-containing layers from indium oxide precursors such as indium alkoxides or indium oxo alkoxides via gas phase deposition. For example U.S. Pat. No. 6,958,300 B2 teaches using at least one metal organo oxide precursor (alkoxide or oxo alkoxide) of the generic formula $M^1_q(O)_x(OR^1)_y$ (q=1-2; x=0-4, y=1-8, $M^1$=metal; e.g. Ga, In or Zn, $R^1$=organic radical; alkoxide when x=0, oxo alkoxide when ≥1) in the production of semiconductors or metal oxide layers by gas phase deposition, for example CVD or ALD. However, all gas phase deposition processes have the disadvantage that they require either i) in the case of a thermal reaction regime, the use of very high temperatures, or ii) in the case of introduction of the required energy for the decomposition of the precursor in the form of electromagnetic radiation, high energy densities. In both cases, it is possible only with a very high level of apparatus complexity to introduce the energy required to decompose the precursor in a controlled and homogeneous manner.

Advantageously, metal oxide layers are thus produced by means of liquid phase processes, i.e. by means of processes comprising at least one process step before the conversion to the metal oxide, in which the substrate to be coated is coated with a liquid solution of at least one precursor of the metal oxide, optionally dried subsequently, and converted. A metal oxide precursor is understood to mean a compound decomposable thermally or with electromagnetic radiation, with which metal oxide-containing layers can be formed in the presence or absence of oxygen or other oxidizing substances. Prominent examples of metal oxide precursors are, for example, metal alkoxides. In principle, the layer can be produced i) by sol-gel processes in which the metal alkoxides used are converted first to gels in the presence of water by hydrolysis and subsequent condensation, and then to metal oxides, or ii) from nonaqueous solution.

The production of indium oxide-containing layers from indium alkoxides from the liquid phase also forms part of the prior art.

The production of indium oxide-containing layers from indium alkoxides via sol-gel processes in the presence of significant amounts of water forms part of the prior art. WO 2008/083310 A1 describes processes for producing inorganic layers or organic/inorganic hybrid layers on a substrate, in which a metal alkoxide (for example one of the generic formula $R^1M-(OR^2)_{y-x}$ or a prepolymer thereof is applied to a substrate, and then the resulting metal alkoxide layer is hardened in the presence of, and reacting with, water. The metal alkoxides usable may include those of indium, gallium, tin or zinc. However, a disadvantage of the use of sol-gel processes is that the hydrolysis-condensation reaction is started automatically by addition of water and is controllable only with difficulty after it has started. When the hydrolysis-condensation process is started actually before the application to the substrate, the gels obtained in the meantime, owing to their elevated viscosity, are often unsuitable for processes for obtaining fine oxide layers. When the hydrolysis-condensation process, in contrast, is started only after application to the substrate by supply of water in liquid form or as a vapour, the resulting poorly mixed and inhomogeneous gels often lead to correspondingly inhomogeneous layers with disadvantageous properties.

JP 2007-042689 A describes metal alkoxide solutions which may contain indium alkoxides, and also processes for producing semiconductor components which use these metal alkoxide solutions. The metal alkoxide films are treated thermally and converted to the oxide layer; these systems too, however, do not afford sufficiently homogeneous films. Pure indium oxide layers, however, cannot be produced by the process described therein.

DE 10 2009 009 338, which was yet to be published at the priority date of the present application, describes the use of indium alkoxides in the production of indium oxide-containing layers from anhydrous solutions. Although the resulting layers are more homogeneous than layers produced by means of sol-gel processes, the use of indium alkoxides in anhydrous systems still has the disadvantage that the conversion of indium alkoxide-containing formulations to indium oxide-containing layers does not give sufficiently good electrical performance of the resulting layer.

DE 10 2009 028 801, which was likewise yet to be published at the priority date of the present application, describes a liquid phase process for producing comparatively improved indium oxide-containing layers from nonaqueous solution, in which an anhydrous composition containing i) at least one indium oxo alkoxide of the generic formula $M_xO_y(OR)_z[O(R'O)_cH]_aX_b[R''OH]_d$ where M=In, x=3-25, y=1-10, z=3-50, a=0-25, b=0-20, c=0-1, d=0-25, R, R', R''=organic radical, X=F, Cl, Br, I and ii) at least one solvent is applied to a substrate, optionally dried, and converted to an indium oxide-containing layer.

Nevertheless, the production of even better indium oxide-containing layers is desirable. It is thus an object of the present invention to provide substances which can be used for production of indium oxide-containing layers (especially of indium oxide layers) with even better electrical performance (especially even better field-effect mobilities $\mu_{FET}$). It would also be desirable to provide substances which can be processed in a simpler manner.

This object is achieved in the present document by the inventive halogenated indium oxo alkoxide of the generic formula $In_7O_2(OH)(OR)_{12}X_4(ROH)_x$ where R=C1-C15-alkyl, C1-C15-alkenyl, C1-C15-alkynyl, C1-C15-alkoxyalkyl, C6-C15-aryl- or C7-C15-alkoxyaryl, X=F, Cl, Br, I and x=0 to 10. Surprisingly, it is additionally possible with these substances to produce particularly high-quality indium oxide-containing layers under air.

These compounds $In_7O_2(OH)(OR)_{12}X_4(ROH)_x$, which have not been described to date in the literature, can be synthesized by means of a conversion of a reaction mixture (A) comprising an indium(III) halide $InX_3$, a sodium or potassium isopropoxide and (preferably dried) isopropanol, preferred removal by filtration of solid (F1) formed as an intermediate and washing with isopropanol to obtain isopropanol-containing wash solutions (B), removal of the isopropanol from the isopropanol-containing solutions (A) and/or (B) to obtain a solid (F2), taking up of the solid (F2) in the alcohol ROH to obtain a mixture (C), preferred performance of one or more filtration steps, and crystallization of the indium oxo alkoxides out of the mixture (C).

In the process according to the invention, the molar ratio of sodium or potassium isopropoxide used to indium(III) halide $InX_3$ is preferably 2.0 to 2.51:1, especially 2.4 to 2.5:1.

Additionally preferably, the molar ratio of the isopropanol used and the indium(III) halide $InX_3$ used is 5 to 3000:1, most preferably 15 to 100:1.

Preferred indium oxo alkoxides are the corresponding chlorides, i.e. corresponding compounds in which X=Cl. These compounds lead to particularly good electrical properties of the corresponding indium oxide-containing layer and can be prepared in a particularly simple manner.

Preference is likewise given to corresponding indium oxo alkoxides in which R=—CH₃, —CH₂CH₃, —CH₂CH₂CH₃, —CH(CH₃)₂, —CH₂CH₂CH₂CH₃, —CH(CH₃)(CH₂CH₃), —CH₂CH₂(CH₃)₂ or —C(CH₃)₃ and which are preparable and processible in a particularly simple manner.

Preference is also given to corresponding indium oxoalkoxy alkoxides in which R=—CH₂CH₂—OCH₃, —CH₂CH₂—OCH₂CH₃, —CH₂CH₂—OCH₂CH₂CH₃, —CH₂CH₂—OCH(CH₃)₂, —CH₂CH₂—OCH₂CH₂CH₂CH₃, —CH₂CH₂—OCH₂CH(CH₃)₂, —CH₂CH₂—OCH(CH₃)(CH₂CH₃) or —CH₂CH₂—OC(CH₃)₃ and which are preparable and processible in a particularly simple manner.

Particularly good yields result in the process according to the invention when the process described is performed with $InCl_3$ and alcohols selected from the group consisting of CH₃OH, HOCH₂CH₃, HOCH₂CH₂CH₃, HOCH(CH₃)₂, HOCH₂CH₂CH₂CH₃, HOCH(CH₃)(CH₂CH₃), HOCH₂CH(CH₃)₂, and HOC(CH₃)₃. The preferred process products formed are $In_7O_2(OH)(OCH_3)_{12}Cl_4(CH_3OH)_x$, $In_7O_2(OH)(OCH_2CH_3)_{12}Cl_4(CH_3CH_2OH)_x$, $In_7O_2(OH)(OCH_2CH_2CH_3)_{12}Cl_4(CH_3CH_2CH_2OH)_x$, $In_7O_2(OH)(OCH(CH_3)_2)_{12}Cl_4(HOCH(CH_3)_2)_x$, $In_7O_2(OH)(OCH_2CH_2CH_2CH_3)_{12}Cl_4(HOCH_2CH_2CH_2CH_3)_x$, $In_7O_2$ (OH)(OCH(CH$_3$(CH$_2$CH$_3$))$_{12}$Cl$_4$(HOCH(CH$_3$)(CH$_2$CH$_3$))$_x$, and In$_7$O$_2$(OH)(OC(CH$_3$)$_3$)$_{12}$Cl$_4$(HOC(CH$_3$)$_3$)$_x$ where x in each case is 0-10.

A particularly preferred inventive indium oxo alkoxide is an indium oxo alkoxide of the generic formula In$_7$($\mu_4$-O)$_2$($\mu_2$-OH)($\mu_1$-OEt)$_3$($\mu_2$-OEt)$_7$($\mu_3$-OEt)$_2$($\mu_1$-Cl)$_4$ which has the structural formula shown in FIG. 1 and which may additionally be present with up to 10 ethanol molecules coordinated in the crystal.

This compound can be prepared as described in the appended example.

The present invention further provides for the use of the inventive indium alkoxides for production of indium oxide-containing layers, and corresponding processes for producing indium oxide-containing layers. The inventive indium oxo alkoxide is suitable in principle for layer production via sputtering processes, via gas phase deposition, for sol-gel processes and for deposition from nonaqueous solution. Particularly suitable for the deposition from nonaqueous solution, however, is the inventive indium oxo alkoxide; the indium oxo alkoxides of the generic formulae are more preferably In$_7$O$_2$(OH)(OCH$_3$)$_{12}$Cl$_4$(CH$_3$OH)$_x$, In$_7$O$_2$(OH)(OCH$_2$CH$_3$)$_{12}$Cl$_4$(CH$_3$CH$_2$OH)$_x$, In$_7$O$_2$(OH)(OCH$_2$CH$_2$CH$_3$)$_{12}$Cl$_4$(CH$_3$CH$_2$CH$_2$OH)$_x$, In$_7$O$_2$(OH)(OCH(CH$_3$)$_2$)$_{12}$Cl$_4$(HOCH(CH$_3$)$_2$)$_x$, In$_7$O$_2$(OH)(OCH$_2$CH$_2$CH$_2$CH$_3$)$_{12}$Cl$_4$(HOCH$_2$CH$_2$CH$_2$CH$_3$)$_x$, In$_7$O$_2$(OH)(OCH(CH$_3$)(CH$_2$CH$_3$))$_{12}$Cl$_4$(HOCH(CH$_3$)(CH$_2$CH$_3$))$_x$, and In$_7$O$_2$(OH)(OC(CH$_3$)$_3$)$_{12}$Cl$_4$(HOC(CH$_3$)$_3$)$_x$ where x=0-10, and very particularly the preferred indium oxo alkoxide of the formula In$_7$($\mu_4$-O)$_2$($\mu_2$-OH)($\mu_1$-OEt)$_3$($\mu_2$-OEt)$_7$($\mu_3$-OEt)$_2$($\mu_1$-Cl)$_4$($\mu_1$-EtOH)$_x$ where x=0-10.

Such a process for producing indium oxide-containing layers by means of deposition from nonaqueous solution is a process in which the substrate to be coated is coated with a liquid nonaqueous solution comprising at least one inventive halogenated indium oxo alkoxide, is optionally subsequently dried and is then converted to an indium oxide-containing layer. Liquid compositions in the context of the present invention are understood to mean those which are in liquid form under SATP conditions ("Standard Ambient Temperature and Pressure"; T=25° C. and p=1013 hPa) and on application to the substrate to be coated. A nonaqueous solution or an anhydrous composition is understood here and hereinafter to mean a solution or formulation comprising not more than 200 ppm of H$_2$O.

The process product of the process according to the invention, the indium oxide-containing layer, is understood to mean a metal- or semimetal-containing layer which comprises indium atoms or ions present essentially in oxidic form. Optionally, the indium oxide-containing layer may also comprise carbon, nitrogen, halogen or alkoxide components from an incomplete conversion or an incomplete removal of by-products formed. The indium oxide-containing layer may be a pure indium oxide layer, i.e. neglecting any carbon, nitrogen, alkoxide or halogen components may consist essentially of indium atoms or ions present in oxidic form, or comprise proportions of further elements which may themselves be present in elemental, oxidic or another form. To obtain pure indium oxide layers, only indium-containing precursors should be used in the process according to the invention, preferably only indium oxo alkoxides and indium alkoxides in addition to the inventive at least one indium oxo alkoxide. In contrast, to obtain layers comprising other metals in addition to the indium-containing precursors, it is also possible to use precursors of metals in the 0 oxidation state (to prepare layers containing further metals in uncharged form) or metal oxide precursors (for example other metal alkoxides or oxo alkoxides).

The present process according to the invention is particularly suitable for producing indium oxide layers when the inventive indium oxo alkoxide is used as the sole metal oxide precursor. Very particularly good layers result when the sole metal oxide precursor corresponds to the formula In$_7$($\mu_4$-O)$_2$($\mu_2$-OH)($\mu_1$-OEt)$_3$($\mu_2$OEt)$_7$($\mu_3$-OEt)$_2$($\mu_1$-Cl)$_4$.

The at least one indium oxo alkoxide is preferably present in proportions of 0.1 to 15% by weight, more preferably 1 to 10% by weight, most preferably 2 to 5% by weight, based on the total mass of the anhydrous composition.

The anhydrous composition further contains at least one solvent, i.e. the composition may contain either one solvent or a mixture of different solvents. Usable with preference in the formulation for the process according to the invention are aprotic and weakly protic solvents, i.e. those selected from the group of the aprotic nonpolar solvents, i.e. of the alkanes, substituted alkanes, alkenes, alkynes, aromatics without or with aliphatic or aromatic substituents, halogenated hydrocarbons, tetramethylsilane, the group of the aprotic polar solvents, i.e. of the ethers, aromatic ethers, substituted ethers, esters or acid anhydrides, ketones, tertiary amines, nitromethane, DMF (dimethylformamide), DMSO (dimethylsulphoxide) or propylene carbonate, and the weakly protic solvents, i.e. the alcohols, the primary and secondary amines and formamide. Solvents usable with particular preference are alcohols, and also toluene, xylene, anisole, mesitylene, n-hexane, n-heptane, tris(3,6-dioxaheptyl)amine (TDA), 2-aminomethyltetrahydrofuran, phenetole, 4-methylanisole, 3-methylanisole, methyl benzoate, ethyl benzoate, ethyl lactate, butyl acetate, N-methyl-2-pyrrolidone (NMP), tetralin and diethyl ether. Very particularly preferred solvents are methanol, ethanol, isopropanol, tetrahydrofurfuryl alcohol, tert-butanol, n-butanol, ethyl lactate, butyl acetate and toluene, and mixtures thereof.

To achieve particularly good printability, the composition used in the process according to the invention preferably has a viscosity of 1 mPa·s to 10 Pa·s, especially 1 mPa·s to 100 mPa·s, determined to DIN 53019 parts 1 to 2 and measured at 20° C. Corresponding viscosities can be established by adding polymers, cellulose derivatives, or SiO$_2$ obtainable, for example, under the Aerosil trade name, and especially by means of PMMA, polyvinyl alcohol, urethane thickeners or polyacrylate thickeners.

The substrate which is used in the process according to the invention is preferably a substrate consisting of glass, silicon, silicon dioxide, a metal oxide or transition metal oxide, a metal or a polymeric material, especially PI or PET.

Indium oxide-containing layers are preferably produced by means of a coating process selected from printing processes (especially flexographic/gravure printing, inkjet printing, offset printing, digital offset printing and screen printing), spraying processes, rotary coating processes ("spin-coating"), dipping processes ("dip-coating"), and processes selected from meniscus coating, slit coating, slot-die coating and curtain coating. The coating process is most preferably a printing process.

After the coating and before the conversion, the coated substrate can additionally be dried. Corresponding measures and conditions for this purpose are known to those skilled in the art.

The conversion to an indium oxide-containing layer can be effected by a thermal route and/or by irradiation with electromagnetic, especially actinic, radiation. Preference is given to converting by a thermal route by means of temperatures of greater than 150° C. Particularly good results can be achieved, however, when temperatures of 250° C. to 360° C. are used for conversion.

Typically, conversion times of a few seconds up to several hours are used.

The thermal conversion can additionally be promoted by injecting UV, IR or VIS radiation or treating the coated substrate with air or oxygen before, during or after the thermal treatment.

The quality of the layer obtained by the process according to the invention can additionally be improved further by a combined thermal and gas treatment (with $H_2$ or $O_2$), plasma treatment (Ar, $N_2$, $O_2$ or $H_2$ plasma), laser treatment (with wavelengths in the UV, VIS or IR range) or an ozone treatment, which follows the conversion step.

The invention further provides indium oxide-containing layers producible by means of the inventive indium oxo alkoxides. Indium oxide-containing layers which are producible from the inventive indium oxo alkoxides and are pure indium oxide layers have particularly good properties.

Owing to the good suitability of the inventive indium oxo alkoxides for the production of indium oxide-containing layers from the liquid phase, the present invention further provides for the use of the inventive indium oxo alkoxides for production of liquid coating compositions. Liquid coating compositions are understood to mean those which are in liquid form under SATP conditions ("Standard Ambient Temperature and Pressure"; T=25° C. and p=1013 hPa) and on application to the substrate to be coated.

The inventive indium oxo alkoxides are additionally advantageously suitable for the production of electronic components, especially the production of transistors (especially thin-layer transistors), displays, RFID tags, circuits, diodes, sensors or solar cells.

The examples which follow are intended to illustrate the subject-matter of the present invention in detail without restriction.

WORKING EXAMPLES

Synthesis of $In_7(\mu_4\text{-}O)_2(\mu_2\text{-}OH)(\mu_1\text{-}OEt)_3(\mu_2\text{-}OEt)_7$ $(\mu_3\text{-}OET)_2(\mu_1\text{-}Cl)_4(\mu_1\text{-}HOEt)_5$ In a 1 l glass round-bottom flask which had been freed of residual moisture, 1.3 g of sodium (56.55 mmol, 2.5 equivalents) were dissolved in 250 ml of isopropanol under a protective gas atmosphere and reflux. To the NaO$^i$Pr solution formed were added 5.0 g (22.6 mmol) of indium(III) chloride (InCl$_3$) in 250 ml of dried isopropanol. The reaction mixture was stirred vigorously under reflux for two hours. After cooling, the solution was filtered and the precipitate was washed twice with 100 ml each time of isopropanol. The combined liquid fractions were concentrated under reduced pressure. The remaining solid was taken up in 200 ml of ethanol (<10 ppm of $H_2O$) and filtered. At approx. 1 week, crystals were formed from the solution at −30° C. (yield approx. 20%). According to single crystal structure analysis, the molecular structure in the crystal corresponds to the formula

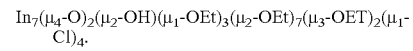

Production of Indium Oxide Layers

A doped silicon substrate with an edge length of about 15 mm and with a silicon oxide coating of thickness approx. 200 nm and finger structures of ITO/gold was coated with 100 µl of a 5% by weight solution of $In_7(\mu_4\text{-}O)_2(\mu_2\text{-}OH)(\mu_1\text{-}OEt)_3(\mu_2\text{-}OEt)_7(\mu_3\text{-}OET)_2(\mu_1\text{-}Cl)_4(\mu_1\text{-}HOEt)_5$ in alcohol (methanol, ethanol or isopropanol) or toluene by spin-coating (2000 rpm). After the coating operation, the coated substrate was heat treated under air at a temperature of 260° C. or 350° C. for one hour.

The inventive coating shows a charge carrier mobility of up to 1.5 cm$^2$/Vs (at gate-source voltage 30 V, source-drain voltage 30 V, channel width 1 cm and channel length 20 µm).

TABLE 1

Charge carrier mobilities

| Solvents | Charge carrier mobility/cm$^2$V$^{-1}$s$^{-1}$ | |
| --- | --- | --- |
| | 260° C. | 350° C. |
| Methanol | 0.2 | 1.0 |
| Ethanol | 0.25 | 1.1 |
| Isopropanol | 0.5 | 1.5 |
| Toluene | 0.1 | 0.8 |

The invention claimed is:

1. A halogenated indium oxo alkoxide of formula $In_7O_2(OH)(OR)_{12}X_4(ROH)_x$
   wherein R is C1-C15-alkyl, C1-C15-alkenyl, C1-C15-alkynyl, C1-C15-alkoxyalkyl, C6-C15-aryl- or C7-C15-alkoxyaryl,
   X is F, Cl, Br, or I, and
   x is from 0 to 10.

2. The indium oxo alkoxide according to claim 1, of formula:

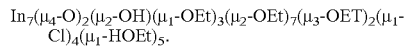

3. A process of preparing the indium oxo alkoxide according to claim 1, the process comprising:
   reacting a reaction mixture comprising an indium(III) halide InX$_3$, a sodium or potassium isopropoxid; and isopropanol and optionally filtering off an intermediate solid and washing the intermediate solid with isopropanol, thereby obtaining an isopropanol-comprising wash solution,
   removing isopropanol from the reaction mixture, the isopropanol-comprising wash solution, or both, thereby obtaining a solid,
   taking up the solid obtained after removing isopropanol in an alcohol ROH, thereby obtaining a mixture,
   optionally filtering the mixture obtained in taking up the solid, and
   crystallizing the indium oxo alkoxide out of the mixture obtained in taking up the solid.

4. The process of claim 3,
   wherein the indium(III) halide InX$_3$ is InCl$_3$ and
   the alcohol is selected from the group consisting of $CH_3OH$, $HOCH_2CH_3$, $HOCH_2CH_2CH_3$, $HOCH(CH_3)_2$, $HOCH_2CH_2CH_2CH_3$, $HOCH(CH_3)(CH_2CH_3)$ and $HOC(CH_3)_3$.

5. A coating, comprising:
   the indium oxo alkoxide according to claim 1.

6. The coating according to claim 5, obtained by a process comprising depositing the coating from nonaqueous solution.

7. A liquid coating composition, comprising:
   the indium oxo alkoxide according to claim 1.

8. An electronic component, comprising:
   the indium oxo alkoxide according to claim 1.

9. The process of claim 3, wherein the process comprises filtering the mixture obtained in taking up the solid.

10. The electronic component of claim 8, wherein the component is a transistor, a display, an RFID tag, a circuit, a diode, a sensor, or a solar cell.

11. The process of claim 3, wherein a molar ratio of the sodium or potassium isopropoxide to the indium(III) halide InX$_3$ in the reacting is from 2.0:1 to 2.51:1.

12. The process of claim 11, wherein the molar ratio of the sodium or potassium isopropoxide to the indium(III) halide $InX_3$ in the reacting is from 2.4:1 to 2.5:1.

13. The process of claim 3, wherein a molar ratio of the isopropanol to the indium(III) halide $InX_3$ in the reacting is from 5:1 to 3000:1.

14. The process of claim 13, wherein the molar ratio of the isopropanol to the indium(III) halide $InX_3$ in the reacting is from 15:1 to 100:1.

15. The process of claim 3, wherein the reaction mixture comprises, as precursors, only precursors that comprise indium.

16. The process of claim 3, wherein the reaction mixture further comprises a precursor comprising a metal other than indium in a 0 oxidation state or a metal oxide precursor comprising a metal other than indium.

17. An anhydrous composition, comprising:
the halogenated indium oxo alkoxide of claim 1, and
a solvent.

18. The composition of claim 17, wherein a content of the alkoxide is from 0.1 to 15% by weight, based on a total mass of the composition.

19. The composition of claim 17, wherein a viscosity of the composition is from 1 to 10 mPa·s determined to DIN 53019 parts 1 to 2 and measured at 20° C.

\* \* \* \* \*